United States Patent
Ruff et al.

(10) Patent No.: US 8,178,497 B2
(45) Date of Patent: May 15, 2012

(54) METHOD OF TREATING HIV IN DRUG RESISTANT NON PLASMA VIRAL RESERVOIRS WITH MONOMERIC DAPTA

(75) Inventors: Michael Ruff, Potomac, MD (US); Candace Pert, Potomac, MD (US)

(73) Assignee: Rapid Pharmaceuticals AG, Zug (CH)

( * ) Notice: Subject to any disclaimer, the term of this patent is extended or adjusted under 35 U.S.C. 154(b) by 1127 days.

(21) Appl. No.: 11/940,147

(22) Filed: Nov. 14, 2007

(65) Prior Publication Data

US 2011/0152179 A1 Jun. 23, 2011

(51) Int. Cl.
*A61K 38/08* (2006.01)
*A61K 38/00* (2006.01)
(52) U.S. Cl. ....................... 514/21.7; 514/3.8
(58) Field of Classification Search ........................ None
See application file for complete search history.

(56) References Cited

U.S. PATENT DOCUMENTS

| | | | |
|---|---|---|---|
| 5,276,016 | A | 1/1994 | Pert et al. |
| 5,834,429 | A | 11/1998 | Pert et al. |
| 5,863,718 | A | 1/1999 | Pert et al. |
| 7,390,788 | B2 | 6/2008 | Pert et al. |
| 7,700,115 | B2 | 4/2010 | Ruff et al. |

OTHER PUBLICATIONS

HIV from Merck Manual, http://www.merckmanuals.com/professional/sec15/ch203/ch203a.html?qt=HIV-a&alt=sh, pp. 1-12. Accessed Jul. 20, 2011.*
Ruff MR, Melendez-Guerrero LM, Yang Q-E, Ho W-Z, Mikovits JW, Pert CB, Ruscetti FA, "Peptide T inhibits HIV-1 infection medicated by chemokine receptor-5 (CCR5)," Antiviral Research, 2001, 52: 63-75.*
Peptide T from ChemBlink, p. 1. Accessed Jul. 20, 2011.*
Polianova et al., Chemokine receptor-5 (CCR5) is a receptor for the HIV entry inhibitor peptide T (DAPTA), Antiviral Res. 2005. 67:83-92.
Ruff et al., CD4 receptor binding peptides that block HIV infectivity cause human monocyte chemotaxis. Relationship to vasoactive intestinal polypeptide. FEBS Lett. 1987. 211:17-22.
Moore et al. In vivo depression of lymphocyte traffic in sheep by VIP and HIV (AIDS)-related peptides. Immunopharmacology. 1988. 16:181-89.
Pert et al. Octapeptides deduced from the neuropeptide receptor-like pattern of antigen T4 in brain potently inhibit human immunodeficiency virus receptor binding and T-cell infectivity. Proc Natl Acad Sci U S A. 1986. 83:9254-9258.
Spisani et al. Chemotactic response of human monocytes to pentapeptide analog derived from immunodeficiency virus protein gp 120. Inflammation. 1990. 14(1):55-60.
Marastoni et al. Synthesis, metabolic stability and chemotactic activity of peptide T and its analogues. J. Peptide Protein Res. 1990. 35:81-88.
Smith et al. Tritiated D-ala-peptide T binding: A pharmacologic basis for the design of drugs which inhibit HIV receptor binding. Drug Development Res. 1988. 15:371-379.
Brenneman et al. Peptide T sequences prevent neuronal cell death produced by the envelope protein (gp120) of the human immunodeficiency virus. Drug Devel Res. 1988. 15:361-369.
Rosi et al. Chemokine receptor 5 antagonist d-ALA-peptide T-amide reduces microglia and astrocyte activation within the hippocampus in a neuroinflammatory rat model of alzheimer's disease. Neuroscience. 2005. 134:671-676.
Kennedy (Ed.) et al. What don't we know? Science. 2005. 309:75-102.
Lusso et al., Cryptic Nature of a Conserved, CD4-Inducible V3 Loop Neutralization Epitope in the Native Envelope Glycoprotein Oligomer of CCR5-Restricted, but Not CXCR4-Using, Primary Human Immunodeficiency Virus Type 1 Strains. J Virol. 2005. 79(11):6957-68.
Ruff et al., Peptide T[4-8] is Core HIV Envelope Sequence Required for CD4 Receptor Attachment. Lancet. 1987. 330(8561):751.

* cited by examiner

*Primary Examiner* — Julie Ha
(74) *Attorney, Agent, or Firm* — Scott W. Houtteman; Kile Park Goekjian Reed & McManus

(57) ABSTRACT

Residual HIV-1 replication reemerges after intensive therapy from location or locations in the body called the drug resistant non-plasma viral reservoir. Methods are disclosed of treating HIV by inhibiting or blocking this reemergence with various monomeric therapeutic peptide compositions including monomeric DAPTA prepared in least 80% trifluoroethanol, with vigorous shaking for at least about 24 hours at about 37° C.

5 Claims, 5 Drawing Sheets

3A

3B

SEQUENCE LISTING

```
<160> NUMBER OF SEQ ID NOS: 1

<210> SEQ ID NO 1
<211> LENGTH: 5
<212> TYPE: PRT
<213> ORGANISM: Human immunodeficiency virus

<400> SEQUENCE: 1

Thr Thr Ser Tyr Thr
1               5
```

METHOD OF TREATING HIV IN DRUG RESISTANT NON PLASMA VIRAL RESERVOIRS WITH MONOMERIC DAPTA

This application is related to U.S. application Ser. No. 11/474,049, filed Jun. 23, 2006, the contents of which are incorporated by reference as if set forth in length herein.

FIELD OF THE INVENTION

Persistently infected, treatment resistant viral reservoirs are a major obstacle to durable treatments, and a cure, for HIV/AIDS. A viral reservoir is a cell type or anatomical site in association with which a replication-competent form of the virus accumulates and persists with more stable kinetic properties than the main pool of actively replicating virus. Thus residual HIV-1 replication continues in the vast majority of patients treated with even the most intensive highly active antiretroviral therapy (HAART) and these reservoirs are the source of virus that remerges upon cessation of therapy. These viruses must come from somewhere inside the body. The inventors have chosen to call the location or locations from where these viruses appear the drug resistant non-plasma viral reservoir.

There are at least two well-described mechanisms for HIV-1 persistence in these patients. These include proviral latency in resting CD4+ T-cells, as well as residual viral replication in cells such as the monocytes/macrophages. In the monocyte population, the CD16 subset is particularly susceptible to HIV infection and can be a source of viral reemergence and re-transmission to T cells. Most focus on viral reservoirs has been on the long-lived T cell reservoir (1), with comparatively much less attention to minor persistently infected cell populations.

Cells of macrophage lineage, including blood monocytes, brain microglia, as well as gut associated lymphoid cells and T cells, play important roles in HIV persistence. Evidence of sequence evolution in blood monocytes, in comparison to resting CD4+ T cells, demonstrates their distinct contribution to plasma viremia. (2) and macrophages are the principle reservoir as T cells become depleted during HIV progression (3). Of particular importance is the inability of current optimized HAART therapies to treat monocyte reservoirs which actively continue to release infectious virus which then spreads throughout the body and brain due to trafficking of these infected cells (2, 4).

Compositions that have dramatically increased potency, reduced aggregation, and increased stability of peptides are useful in the therapeutic treatment of persistant HIV cellular viral reservoirs, prevention of neuronal apoptosis in AIDS, and reduced inflammation. Specifically compositions having at least one peptide prepared in a manner which retains and enhances biological acticvity.

BACKGROUND AND INFORMATION

CD4 T cells and monocyte/macrophages (M/M) play an important role in all phases of human immunodeficiency virus type 1 (HIV-1) infection, acting as vehicles for virus dissemination in the body and representing the major reservoir for long term persistence of HIV-1 during highly active anti-retroviral therapy (HAART) (5-7). Elimination of these viral reservoirs are an important treatment goal not achieved by current optimized highly active antiviral therapies. M/M continue to shed infectious virus, even with effective HAART therapy, and thus are a source of reinfection and evolution of treatment resistant viral strains.

Microglia, local differentiated M/M, are the main source of virus in the brain, whose pathogenic secretory products cause neuro-AIDS (8, 9). HIV-1 entry into cells occurs after binding of the viral envelope glycoprotein gp120 to specific chemokine receptors in conjunction with the CD4 receptor (10, 11) CCR5 in particular is the principal coreceptor for the HIV-1 strains that are transmitted between individuals and which predominate during the early years of infection and predominate in the brain where they cause the manifestation of neuro-AIDS, via infection of CCR5 expressing monocytes and microglia (12, 13). M/M and microglia are infected primarily by CCR5 using HIV strains. CCR5 is also expressed on neuronal cell lines and astrocytes in the brain and, whereas it is known that neuronal cells are usually not productively infected by HIV-1, in vitro studies have shown that natural ligands of CCR5 protect neurons from gp120-mediated apoptosis (14-16). Drugs which block CCR5 receptors on brain cells would be useful treatments to prevent neuronal apoptosis, a cause of Neuro-AIDS and dementia or mental impairment. Furthermore antibodies that block gp120 binding to CCR5 would be useful as a broadly neutralizing AIDS vaccine as CCR5 co-receptor use is an invariant feature of viral strains that establish initial infection.

Dala1-peptide T-amide (DAPTA) is a synthetic peptide derived from HIV gp120 that functions as a viral entry inhibitor by blocking gp120 binding to CCR5 (13, 17, 18). Freshly prepared, compared to stored, solutions of this small peptide suppresses the infection of peripheral blood monocytes in vitro (17) suggesting that blocking infection of monocytes in patients would prevent and reduce the population of infected differentiated M/M which are resistant to current treatments and which form a reservoir of infected differentiated M/M in patients MM reservoirs are sources of infection for T cells which sustain low level viral replication in the face of therapy leading to resistance development and treatment failure. Current HAART therapies do not effectively treat the monocyte.macrophage reservoirs (2, 19, 20).

A small clinical trial of DAPTA has shown mixed results, having some antiviral benefits in the monocytes, but failing to reduce plasma viral load, the main endpoints of the study. An earlier multi-site, placebo-controlled trial conducted by the NIH had also failed to achieve significance on the main trial endpoints, neurocognitive benefits (21), as did a placebo-controlled trial of peptide T for HIV associated neuropathhic pain (22). An analysis of frozen stored plasma samples conducted by the NIMH in the early-1990's from the randomized double-blind placebo-controlled trial of DAPTA for HIV-associated cognitive impairment (21) found a barely significant reduction in viral load (0.54 log 10, p=. 037), a modest effect, not comparable to the −2 log 10 reductions of viral load offered by several current anti-viral therapies. These marginal clinical benefits were inexplicable in the context of the many successful in vitro studies and an explanation was sought. Patient reports of sporadic gel foiniation in trial nasal sprayers suggested an explanation focused on the bio-physical character of the peptide drug. This sporadic change in physical state was unexpected and had not been revealed in many scientific studies which had used peptide T, and had not been reported in any of the clinical articles. An analysis of clinical trial formulated drug according to U.S. Pat. Nos. 5,276,016 and 5,834,429 revealed substantial aggregation and loss of biological activity, in a variable manner, dependent upon individual storage conditions and temperature. Further direct experimentation showed that DAPTA and peptide T quickly formed aggreagates in solution, which over time formed fibrils, and that both aggregates and fibril forms were devoid of biological activity. Therefore reduction to practice

SUMMARY OF THE INVENTION

The present invention relates to compositions and methods of preparation of monomeric Dala1-peptide T-NH2, Peptide T, and related peptide analogs in which pre-existing seed aggregates introduced as part of the normal solid-phase synthesis and removal of solvents are removed, and the preparation of solutions suitable for human treatment uses that do not form aggregates upon storage is possible. Furthermore, the present invention provides for compositions that when administered preclude or reduce aggregation thereby increasing the shelf-life of the therapeutic or increasing the range of conditions, such as temperature or aggregation that may be tolerated without causing harm to the functional properties of the therapeutic. Furthermore, peptide therapeutics like DAPTA and peptide T and analogs, when prepared in such a manner evince enhanced potencies of 100-1000 fold by tests of in vitro antiviral effect on monocyte/macrophages, indicating a treatment use for lowering or eliminating persistent viral reservoirs by blocking CCR5. These compositions of monomeric DAPTA, peptide T and analogs would also prevent neuronal apoptosis, a cause of AIDS dementia, and down-regulation of CCR5, leading to reduced inflammation.

DETAILED DESCRIPTION OF THE INVENTION

Figure 1:
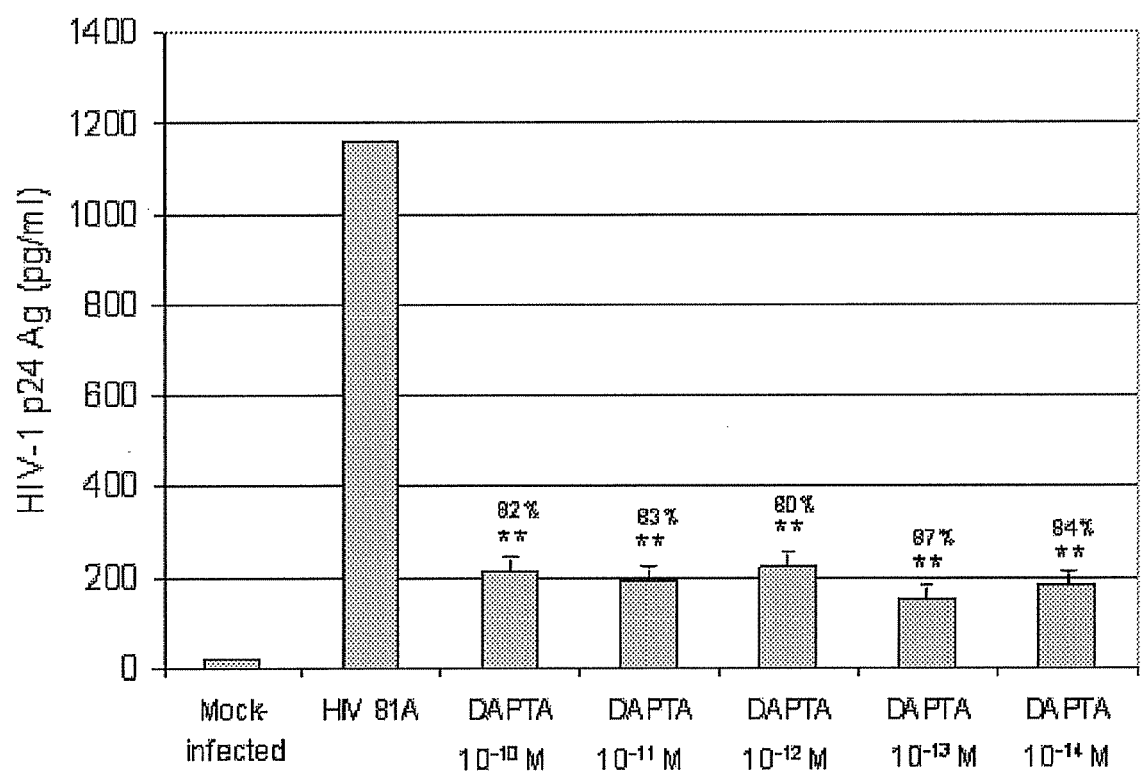
FIG. 1 illustrates the results of DAPTA treatment on HIV infected M/M cells.

The present invention may be more readily understood by reference to the following specific embodiments and examples A method for reducing or preventing the aggregation of a therapeutically active peptide, polypeptide or variant thereof upon reconstitution by admixing a therapeutically active peptide, polypeptide or variant thereof and a fluorinated organic solvent, removing the fluorinated organic solvent, and reconstituting the therapeutically active peptide, polypeptide or variant thereof with an aqueous solution, thereby increasing the biological activity of the therapeutically active peptide, polypeptide or variant thereof by eliminating minor contaminant aggregates which form seeds that then rapidly promote further aggregation leading to fibril formation and loss of bioactivity. The fluorinated organic solvents include but are not limited to trifluoroethanol (TFE) and 1,1,1,3,3,3,-hexafluoro-2-propanol (HFIP). Concentrations of fluorinated organic solvents, where TFE is a favored embodiment, comprise 80 to 100%. Although use of the lower TFE concentration is possible, use of 100% is favored as it avoids an artifact introduced by drying which would partition some of the peptide into the residual water phase at the high concentrations which promote aggregation. Concentrations of peptide should be maintained at 5 mg/ml or less in the final reconstitution in water, in the absence of salts, especially NaCl, which is commonly used to prepare physiological solutions.

The invention also provides a method for increasing the biological activity, promoting storage stability, and preventing or eliminating aggragation of a therapeutically active peptide, polypeptide or variant thereof by reconstitution in a fluorinated organic solvent with vigorous shaking at warm temperatures, from 37 to 56 C for 24 hours or longer.

The invention also provides a method for increasing the biological activity of a therapeutically active peptide, polypeptide or variant thereof upon reconstitution by admixing a therapeutically active peptide, polypeptide or variant thereof and a fluorinated organic solvent, shaking in the warm, removing the fluorinated organic solvent, and reconstituting the therapeutically active peptide, polypeptide or variant thereof with an aqueous solution, thereby increasing the biological activity of the therapeutically active peptide, polypeptide or variant thereof.

Still, the invention provides a method for reducing or preventing fibrillar formation of a therapeutically active peptide, polypeptide or variant thereof upon reconstitution by admixing a therapeutically active peptide, polypeptide or variant thereof and a fluorinated organic solvent, removing the fluorinated organic solvent, and reconstituting the therapeutically active peptide, polypeptide or variant thereof with an aqueous solution, thereby increasing the biological activity of the therapeutically active peptide, polypeptide or variant thereof.

The therapeutically active peptide, polypeptide or variant thereof of the invention includes but is not limited to Peptide T or an analog thereof, including D-ala$^1$-Peptide T-amide, D-ala$^1$-Peptide T lacking an amide at the C-terminus, D-ala$^1$Thr$^8$-Peptide T amide, Vasoactive Intestinal peptide (VIP), Thr-Thr-Ser-Tyr-Thr (Seq. ID NO. :1). Peptides in the normal L form, may be prepared and used in this manner.

Monomeric DAPTA Inhibits Replication of HIV-1 CCR5-Using Strains in Macrophages.

DAPTA was prepared by the methods described herein to be free of aggregates. These aggregated peptide forms are themselves biologically inactive due to their inability to bind to CCR5, and their presence in minute amounts in stored solutions promotes further aggregation and fibril formation, with concomitant loss of biological activity and clinical effect. Standard and typical formulations used in previous trials (21), or laboratory studies (23) have lost activity, or been devoid of activity. The reasons for variable and negative results have been confounding and until now unknown, with pernicious and deleterious effects for meeting treatment needs in HIV/AIDS.

Viral replication and production in HIV-infected M/M treated with DAPTA was assessed 14 and 21 days after infection for p24 antigen production. A representative experiment is shown in FIG. 1.

The CCR5-using HIV-1 strain, 81A had p24 gag antigen production of control M/M cultures reduced ~80% by doses of monmeric DAPTA as low as $10^{-14}$ M (FIG. 1). DAPTA had no effect on HIV-1 p24 antigen production in M/M infected by CXCR4-using (X4) strains, HIV-1 IIIB (data not shown). These results are some 100-100,000 fold lower than described in earlier reports. Thus Sodroski failed to find antiviral effects of DAPTA at doses as high as $10^{-7}$ M (23), and effective in vitro doses were typically reported to be $10^{-12}$ M to $10^{-9}$ M (17). Thus this improved formulation enhanced in vitro potency by 100 to 100.000-fold. Preparation and storage of DAPTA, without modifications to prevent aggregation, can rapidly result in orders of magnitude loss of potency,

Monomeric DAPTA Induced CCR5 Binding in Human Primary Macrophages

Figure 2:
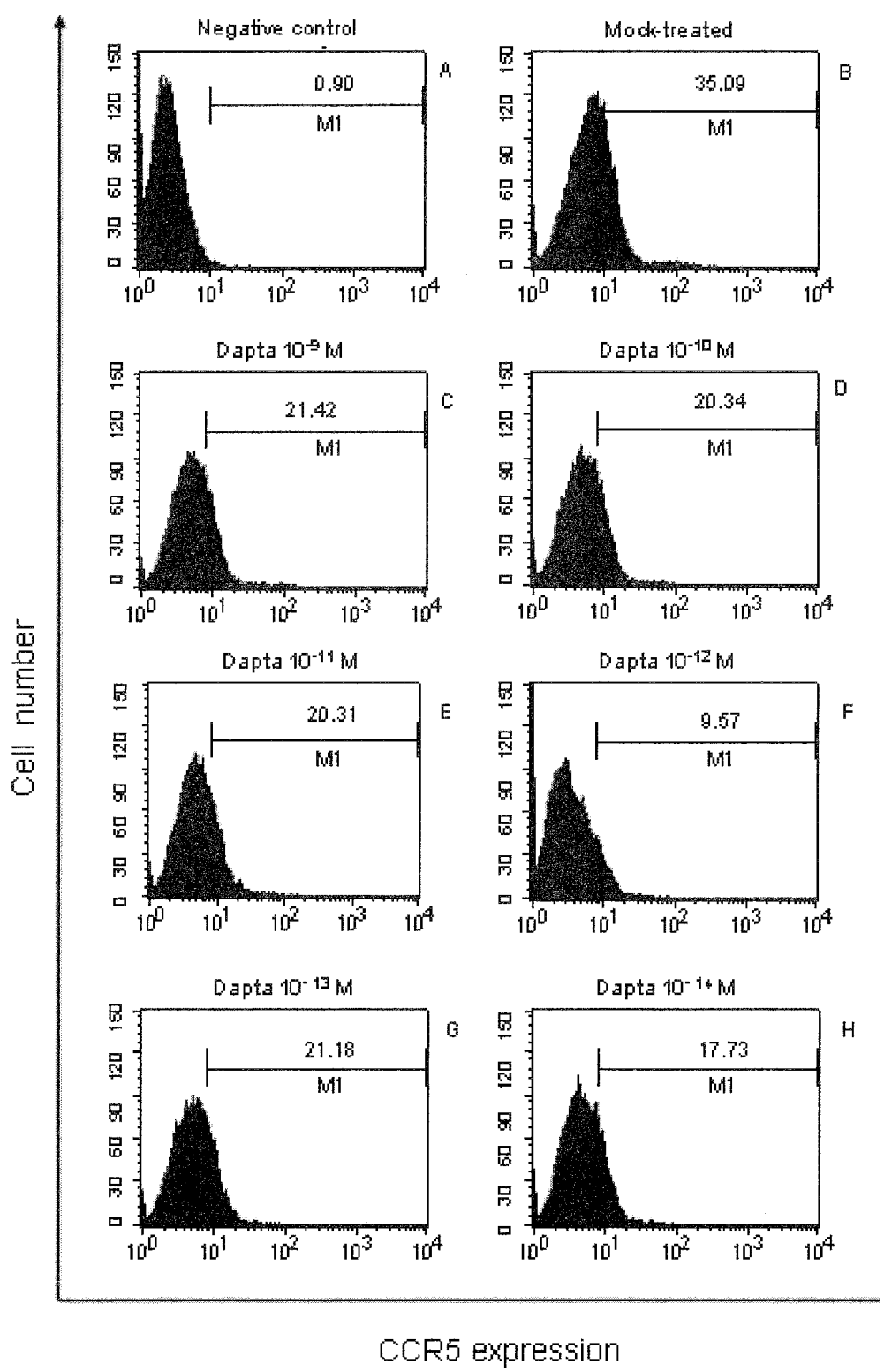
FIG. 2 confirms DAPTA binding is specific for CCR5 by illustrating a competition for CCR5 binding between CCR5-FITC antibody and DAPTA.

To confirm that monomeric DAPTA binding is specific for CCR5, a competition experiment between CCR5-FITC antibody and DAPTA in M/M was done. Flow cytometric analysis showed that 20% of DAPTA treated M/M are CCR5+ positive. Treatment with monomeric DAPTA reduced CCR % expression to 9% with $10^{-12}$ M DAPTA, compared with 35% of mock-treated M/M (FIG. 2) ($p \leq 0.001$).

Overall, the inhibition of CCR5-binding by several DAPTA doses is about 43% and reaches a maximum of 73% with $10^{-12}$ M. These results clearly indicate that DAPTA reduced the CCR5 antibody binding to the receptor in M/M by down-regulating receptor expression. DAPTA compositions which did not have reduced or absent aggregates failed to down-regulate CCR5 expression (data not shown).

Monomeric DAPTA Reduces Levels of HIV-1 DNA in Human Primary Macrophages

Figure 3:
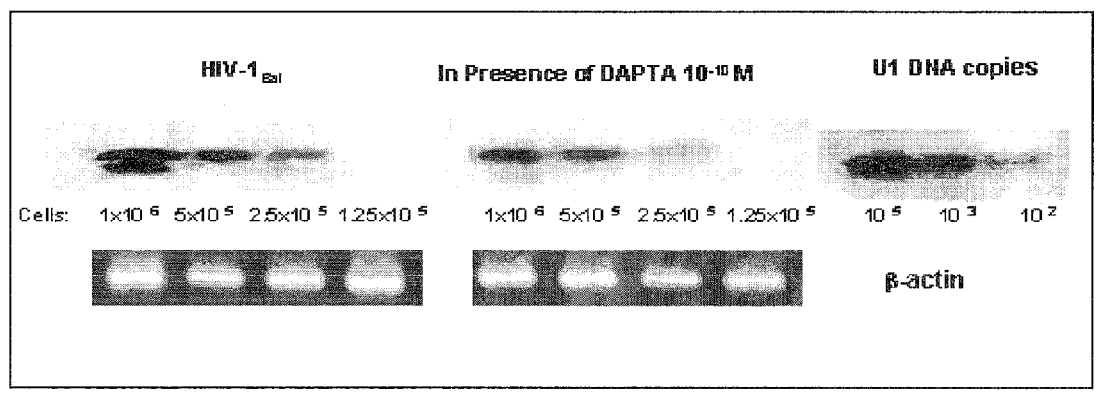
FIGS. 3A-B illustrates peptide DAPTA treatment reduces DNA formation in M/M cells.
Figure 3:
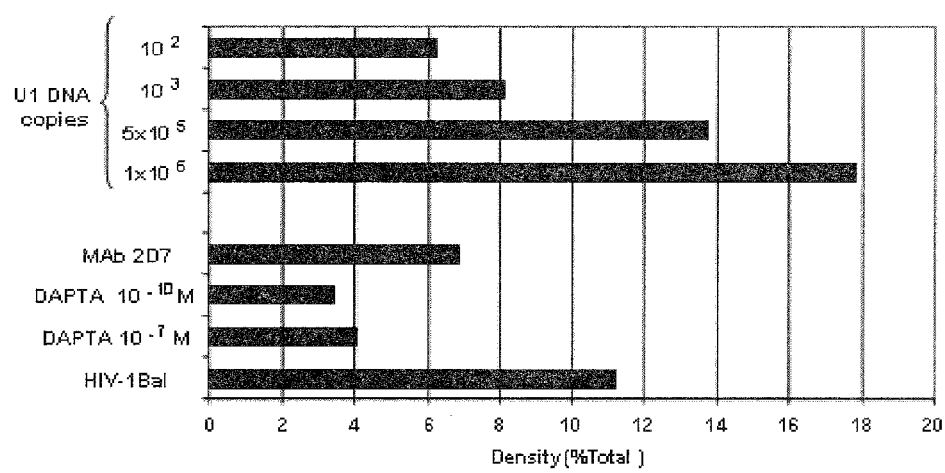

To further prove that monomeric peptide DAPTA blocks virus infection with increased potency, M/M were analyzed for HIV-1 DNA formation. Eighteen hours postinfection, genomic DNA was extracted and two-fold dilution of cell equivalents (range $1 \times 10^6$-$1.25 \times 10^5$) were amplified in an inverse/nested PCR specific for a conserved gag region of the viral genome. Semi-quantitative analyses of HIV-1 DNA in M/M were performed by comparison of DNA amplification products from infected cells, standardized by PCR for β-actin, to standards of amplified U1 DNA copies and cell numbers. The UN-SCAN IT-gel software (Silk Scientific Inc.) was used to determine band densities (FIG. 3A). We observed that HIV-1 DNA per $2.5 \times 10^5$ cells declined with 64% in the presence of peptide DAPTA ($10^{-7}$ M) and with 70% in the presence of $10^{-9}$ M peptide DAPTA, compared with not-treated cells. In the absence of peptide DAPTA or 2D7 mAb, approximately $1 \times 10^4$ HIV-1 copies were presented per $10^5$ M/M (i.e. 0.1 copy×M/M). The inhibition of HIV-1 DNA formation detected in M/M in the presence of mAb 2D7 at the maximum amount of 3 μg/ml was approximately 39% (FIG. 3B). In conclusions, these data indicate that monomeric DAPTA inhibits productive infection in M/M by blocking specifically the CCR5 dependent entry with a potency greater than that of the specific anti-CCR5 antibody 2D7. The results suggest use as a therapy for treatment resistant monocyte/macrophage or T cell infection in HIV/AIDS.

Figure 4:
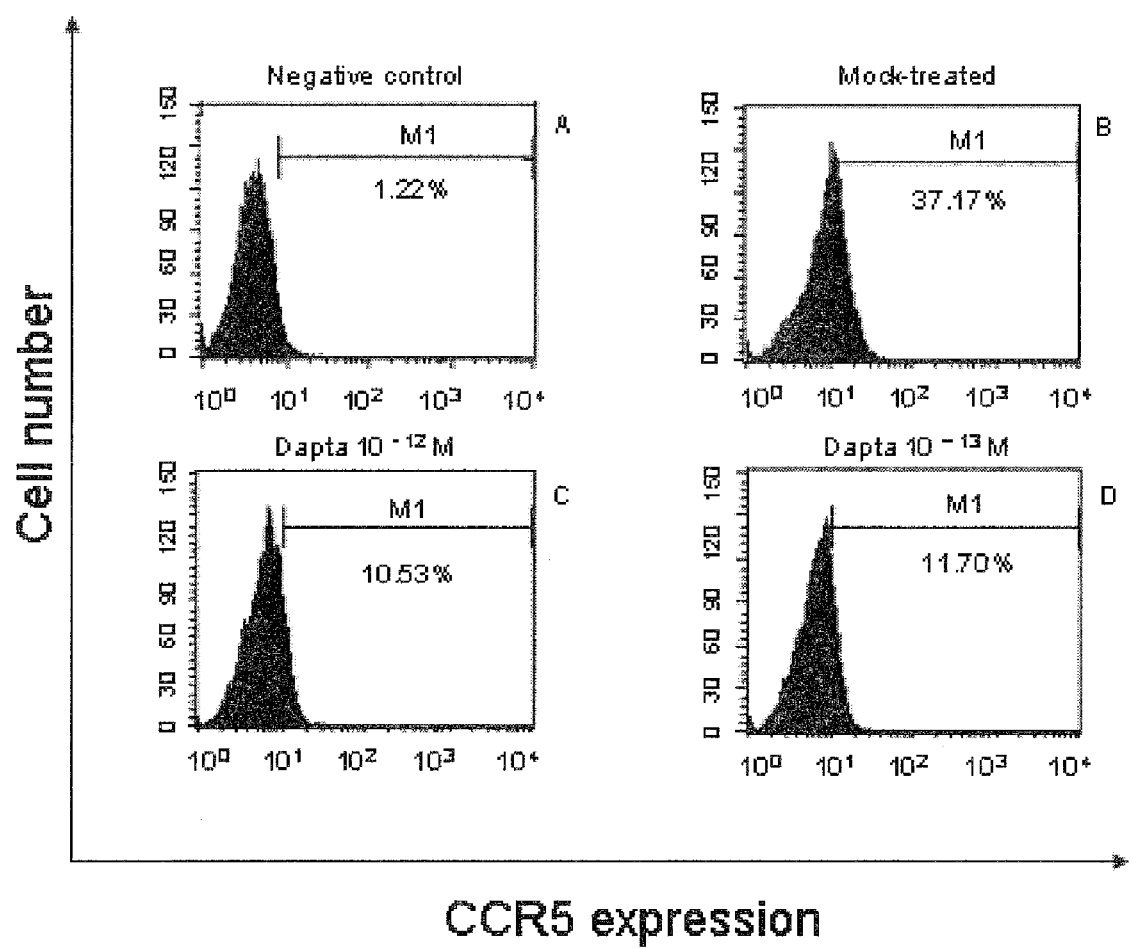
FIG. 4 illustrates DAPTA treatment lowers CCR5 expression on neuronal cell lines

MONOMERIC DAPTA Effects on CCR5 Binding and gp120-Induced Apoptosis in Neuronal Cell Lines To assess CCR5 expression on surface of neuronal cell lines, SK-N-SH were stained with 2D7 mAb in presence or in absence of DAPTA (at different doses) and TAK-779. SK-N-SH line has the potential of differentiating to neural cells in the presence of retinoic acid, and it has been used as a model of primary neurons. The results indicate that CCR5 expression in these differentiated cells is limited and further reduced in the presence of DAPTA; indeed an inhibition of CCR5 expression of 68.5% and 72% in presence of $10^{-13}$M and $10^{-12}$M DAPTA concentration respectively was observed in comparison with unexposed SK-N-SH (FIG. 4) (p<0.001). In the presence of TAK-779 ($1.8 \times 10^{-6}$ M) the inhibition is about 61%. Thus, monomeric DAPTA is considerably more potent than TAK-779 to downmodulate CCR5 coreceptor expression in a neuronal cell line.

Figure 5:
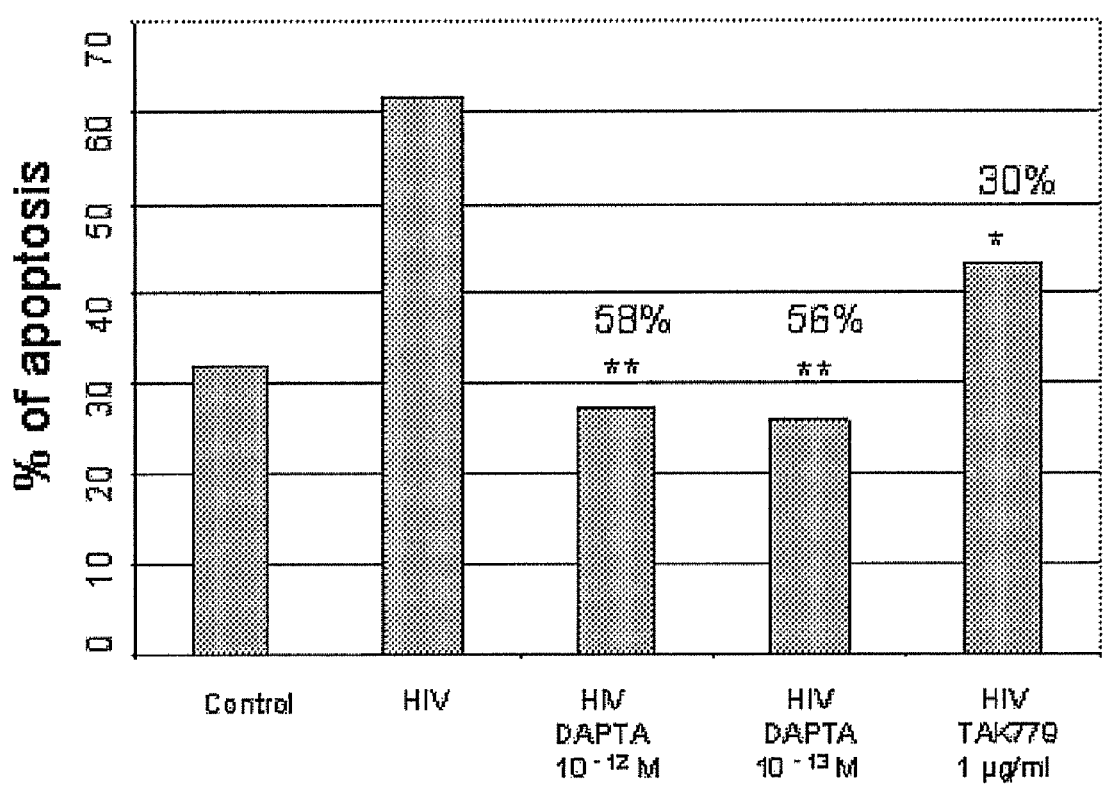
FIG. 5 illustrates DAPTA significantly reduces levels of apoptosis caused by HIV.

Finally, we exposed differentiated SK-N-SH cells to the R5 HIV-1 strain BaL, in the presence or absence of monomeric DAPTA, and assessed neuronal apoptosis. Time-course studies revealed that cell apoptosis in this cellular line occurred between 5 and 6 days after addition of the virus. Thus results will be shown at day 5. In particular, when SK-N-SH were incubated with HIV-$1_{BaL}$, a dramatic reduction of cell viability was seen by FACS analysis. The cytopathic effect, observed in SK-N-SH exposed to R5 HIV-1 released from infected M/M, was mainly related to apoptosis. Indeed, FACS analysis showed apoptosis in 60% of SK-N-SH cells exposed to HIV-$1_{BaL}$ compared to 28% and 26% observed in DAPTA $10^{-3}$M and $10^{-12}$M treated cells, respectively. To compare the anti-apoptotic effect of monomeric DAPTA with other CCR5-binding molecules, we also tested the CCR5 antagonist TAK-779. SK-N-SH cells treated with $1.8 \times 10^{-6}$ M TAK-779 (a concentration able to strongly inhibit virus replication in M/M) resulted in only a 30% inhibition of apoptosis compared with the cells not treated with TAK-779 (FIG. 5). These data also indicated that monomeric DAPTA is more potent in preventing the neuronal apoptosis compared to TAK-779 and has increased potency compared to non-monomeric peptide preparations.

In treating HIV infection, useful peptide concentrations in the composition can range from about 5 mg/ml to about 0.00005 mg/ml. Effective blood plasma levels are expected to range from about $10^{-9}$M to about $10^{-17}$M. The inventors specifically contemplate the use of all concentrations within these ranges depending on the surrounding circumstances. For example, treated patients can be in different stages of infection, have different genetic or physiologic backgrounds. Different concentration levels will be optimal as one balances drug potency and adverse side effects.

References

1. Blankson, J. N., D. Persaud, and R. F. Siliciano. 2002. The challenge of viral reservoirs in HIV-1 infection. *Annu Rev Med* 53:557-593.
2. Crowe, S., T. Zhu, and W. A. Muller. 2003. The contribution of monocyte infection and trafficking to viral persistence, and maintenance of the viral reservoir in HIV infection. *J Leukoc Biol.* 74:635-641.
3. Igarashi, T., C. R. Brown, Y. Endo, A. Budder-White, R. Plishka, N. Bischofberger, V. Hirsch, and M. A. Martin. 2001. Macrophage are the principal reservoir and sustain high virus loads in rhesus macaques after the depletion of CD4+ T cells by a highly pathogenic simian immunodeficiency virus/HIV type 1 chimera (SHIV): Implications for HIV-1 infections of humans. *Proc Natl Acad Sci USA.* 98:658-663.
4. Pomerantz, R. J. 2002. Reservoirs of human immunodeficiency virus type 1: the main obstacles to viral eradication. *Clin Infect Dis.* 34:91-97.
5. Aquaro, S., R. Calio, J. Balzarini, M. C. Bellocchi, E. Garaci, and C. F. Perno. 2002. Macrophages and HIV infection: therapeutical approaches toward this strategic virus reservoir. *Antiviral Res.* 55:209-225.
6. Perelson, A. S., P. Essunger, Y. Cao, M. Vesanen, A. Hurley, K. Saksela, M. Markowitz, and D. D. Ho. 1997. Decay characteristics of HIV-1-infected compartments during combination therapy. *Nature.* 387:188-191.
7. Sharkey, M. E., I. Teo, T. Greenough, N. Sharova, K. Luzuriaga, J. L. Sullivan, R. P. Bucy, L. G. Kostrikis, A. Haase, C. Veryard, R. E. Davaro, S. H. Cheeseman, J. S. Daly, C. Bova, R. T. r. Ellison, B. Mady, K. K. Lai, G. Moyle, M. Nelson, B. Gazzard, S. Shaunak, and M. Stevenson. 2000. Persistence of episomal HIV-1 infection intermediates in patients on highly active anti-retroviral therapy. *Nat Med.* 6:76-81.
8. Brenneman, D. E., G. L. Westbrook, S. P. Fitzgerald, D. L. Ennist, K. L. Elkins, M. R. Ruff; and C. B. Pert. 1988. Neuronal cell killing by the envelope protein of HIV and its prevention by vasoactive intestinal peptide. *Nature.* 335:639-642.

9. Lipton, S. A., D. E. Brenneman, F. S. Silverstein, E. Masliah, and L. Mucke. 1995. gp120 and neurotoxicity in vivo. *Trends Pharmacol Sci.* 16(4):122.
10. Kaul, M., G. A. Garden, and S. A. Lipton. 2001. Pathways to neuronal injury and apoptosis in HIV-associated dementia. *Nature.* 410:988-994.
11. Berger, E. A., P. M. Murphy, and J. M. Farber. 1999. Chemokine receptors as HIV-1 coreceptors: roles in viral entry, tropism, and disease. *Annu Rev Immunol.* 17:657-700.
12. Douek, D. C., L. J. Picker, and R. A. Koup. 2003. T cell dynamics in HIV-1 infection. *Annu Rev Immunol.* 21:265-304.
13. Polianova, M. T., F. W. Ruscetti, C. B. Pert, and M. R. Ruff. 2005. Chemokine receptor-5 (CCR5) is a receptor for the HIV entry inhibitor peptide T (DAPTA). *Antiviral Res.* 67:83-92.
14. Gabuzda, D., and J. Wang. 2000. Chemokine receptors and mechanisms of cell death in HIV neuropathogenesis. *J Neurovirol.* 6 Suppl 1:S24-32.
15. Kaul, M., and S. A. Lipton. 1999. Chemokines and activated macrophages in HIV gp120-induced neuronal apoptosis. *Proc Natl Acad Sci USA.* 96:8212-8216.
16. Brenneman, D. E., J. Hauser, C. Y. Spong, T. M. Phillips, C. B. Pert, and M. Ruff. 1999. VIP and D-ala-peptide T-amide release chemokines which prevent HIV-1 GP120-induced neuronal death. *Brain Res.* 838:27-36.
17. Ruff, M. R., L. M. Melendez-Guerrero, Q. E. Yang, W. Z. Ho, J. W. Mikovits, C. B. Pert, and F. A. Ruscetti. 2001. Peptide T inhibits HIV-1 infection mediated by the chemokine receptor-5 (CCR5). *Antiviral Res.* 52:63-75.
18. Redwine, L. S., C. B. Pert, J. D. Rone, R. Nixon, M. Vance, B. Sandler, M. D. Lumpkin, D. J. Dieter, and M. R. Ruff. 1999. Peptide T blocks GP120/CCR5 chemokine receptor-mediated chemotaxis. *Clin Immunol.* 93:124-131.
19. Sonza, S., H. P. Mutimer, R. Oelrichs, D. Jardine, K. Harvey, A. Dunne, D. F. Purcell, C. Birch, and S. M. Crowe. 2001. Monocytes harbour replication-competent, non-latent HIV-1 in patients on highly active antiretroviral therapy. *AIDS.* 15:17-22.
20. Lambotte, O., Y. Taoufik, M. G. de_Goer, C. Wallon, C. Goujard, and J. F. Delfraissy. 2000. Detection of infectious HIV in circulating monocytes from patients on prolonged highly active antiretroviral therapy. *J Acquir Immune Defic Syndr.* 23:114-119.
21. Heseltine, P. N., K. Goodkin, J. H. Atkinson, B. Vitiello, J. Rochon, R. K. Heaton, E. M. Eaton, F. L. Wilkie, E. Sobel, S. J. Brown, D. Feaster, L. Schneider, W. L. Goldschmidts, and E. S. Stover. 1998. Randomized double-blind placebo-controlled trial of peptide T for HIV-associated cognitive impairment. *Arch Neurol.* 55:41-51.
22. Simpson, D. M., D. Dorfman, R. K. Olney, G. McKinley, J. Dobkin, Y. So, J. Berger, M. B. Ferdon, and B. Friedman. 1996. Peptide T in the treatment of painful distal neuropathy associated with AIDS: results of a placebo-controlled trial. The Peptide T Neuropathy Study Group. *Neurology.* 47:1254-1259.
23. Sodroski, J., M. Kowalski, T. Dorfman, L. Basiripour, C. Rosen, and W. Haseltine. 1987. HIV envelope-CD4 interaction not inhibited by synthetic octapeptides [letter]. *Lancet.* 1:1428-1429.

We claim:

1. A method of treating HIV infection in drug-resistant non-plasma viral reservoirs comprising:

administering a pharmaceutically effective dose of a monomeric therapeutic peptide composition comprising D-ala$^1$-Peptide T-amide to a patient;

wherein the monomeric peptide has an α-helical secondary structure, and wherein said therapeutic composition treats HIV infection in said drug-resistant reservoir.

2. The method of treating HIV infection as defined in claim 1 wherein said drug-resistant non-plasma viral reservoir is selected from the group consisting of brain cells, non-brain neural cells, monocytes, T-cells, GALT (gut-associated lymphoid tissue) and macrophage cells.

3. The method of treating HIV infection as defined in claim 1 wherein said pharmaceutically effective dose is results in a plasma peptide concentration of about $10^{-17}$ M to about $10^{-9}$ M.

4. The method of treating HIV infection as defined in claim 1 wherein said therapeutic composition has a peptide concentration in the range of about 0.00005 mg/ml to about 5.0 mg/ml.

5. A method of treating HIV infection by inhibiting viral entry into cells comprising:

administering a pharmaceutically effective dose of a monomeric therapeutic peptide composition comprising D-ala$^1$-Peptide T-amide to a patient;
wherein the monomeric peptide has an α-helical secondary structure, and wherein said therapeutic composition lowers the number of CCR5 receptors on cell surfaces, inhibits viral entry into cells and thus treat HIV infection.

* * * * *